United States Patent [19]
Habermeyer

[11] Patent Number: 6,066,107
[45] Date of Patent: May 23, 2000

[54] APPARATUS FOR THE SURROUNDIVE FIXATION OF EXTREMITIES

[76] Inventor: Peter Habermeyer, Oberfoehringer Str. 27, 8000 Munich 81, Germany

[21] Appl. No.: 08/275,091

[22] Filed: Jul. 14, 1994

Related U.S. Application Data

[63] Continuation of application No. 07/812,874, Dec. 20, 1991, abandoned, which is a continuation of application No. 07/474,025, Jun. 4, 1990, abandoned.

[30] Foreign Application Priority Data

Aug. 5, 1988 [DE] Germany ............................ 38 26 704
Dec. 30, 1988 [DE] Germany ............................ 38 44 381

[51] Int. Cl.$^7$ ............................................ A61F 5/05
[52] U.S. Cl. .............................. 602/6; 602/13; 128/847
[58] Field of Search .................................... 128/83, 87 B, 128/89 R, 90, 160, 165, 846, 847, DIG. 15, DIG. 20; 36/119; 602/5, 6, 13

[56] References Cited

U.S. PATENT DOCUMENTS

| | | | |
|---|---|---|---|
| 3,580,248 | 5/1971 | Larson | 602/13 X |
| 3,631,854 | 1/1972 | Fryer | 128/DIG. 20 |
| 3,643,656 | 2/1972 | Young et al. | 602/13 |
| 3,701,349 | 10/1972 | Larson | 602/13 X |
| 3,745,998 | 7/1973 | Rose | 128/DIG. 15 |
| 3,760,056 | 9/1973 | Rudy | 128/90 X |
| 3,762,404 | 10/1973 | Sakita | 128/DIG. 20 |
| 4,654,986 | 4/1987 | George | 36/119 |
| 4,657,003 | 4/1987 | Wirtz | 128/89 R |
| 4,727,865 | 3/1988 | Hill-Byrne | 602/6 |
| 4,730,403 | 3/1988 | Walkhoff | 36/119 |
| 4,744,157 | 5/1988 | Dubner | 36/119 |

FOREIGN PATENT DOCUMENTS 1531268 11/1978 United Kingdom ................... 602/13

*Primary Examiner*—Danton D. DeMille
*Attorney, Agent, or Firm*—Townsend and Townsend and Crew LLP

[57] ABSTRACT

An apparatus is described for the surroundive fixation of extremities in which a double-walled cuff-forming cushion is used which can be deformed into a sleeve, which can be made vacuum-tight and which is provided with a evacuation valve. A plurality of loose particulate filling bodies is provided in the inner space of the cuff-forming cushion between the two walls and the cushion can be consolidated by evacuation into a stiff stable structure.

4 Claims, 3 Drawing Sheets

APPARATUS FOR THE SURROUNDIVE FIXATION OF EXTREMITIES

This is a Continuation of Ser. No. 07/812,874, filed Dec. 20, 1991, now abandoned, which is a continuation of Ser. No. 07/474,025, filed Jun. 4, 1990, now abandoned.

BACKGROUND OF THE INVENTION

The invention relates to an apparatus for the surroundive fixation of extremities and regions of extremities, in particular for treating extremity fractures in the region of the lower leg, thigh, lower arm, and upper arm and also for use in ski boots and the like.

For the treatment of extremity fractures plaster casts or their modern variants in the form of plastic casts are normally applied. The application of such casts requires however not only considerable skill and corresponding effort for the personnel, but rather also frequently leads to pressure points which are extremely disturbing for the patient due to edges or projections at the inner side of the plaster or plaster cast. After the resetting of the particular fracture the patient is subjected to the painful phase of winding of the bandages and waiting for the setting of the plaster. Finally, it is generally necessary with the known plaster or plastic casts to change this plaster or plastic cast when swelling of the relevant limb recedes during the course of treatment of the fracture. This is also involved and again unpleasant procedure for the patient.

SUMMARY OF THE INVENTION

The object of the invention is to form an apparatus of the initially named kind in such a way that the indicated disadvantages of plaster and plastic casts can be avoided and so that a simple surroundive fixation of extremities is possible, which can be rapidly effected, which does not lead to any pressure points, which is effective practically without delay, and which can be released simply and can at once be newly applied. Moreover, the apparatus should ensure a precise but nevertheless pressure-free support within ski boots and the like.

This object is essentially solved in accordance with the invention by a double walled cuff-forming cushion which can be formed into a sleeve, which is made vacuum-tight and which is provided with at least one evacuation valve, with a plurality of filling bodies which are movable relative to one another being provided in the interior space of the cuff cushion between the two walls.

The cuff-forming cushion which can be formed into a sleeve and which can thus be applied tightly and in fitting manner to the portion of the limb to be treated becomes hard and of stable shape in the shape provided during the application process through evacuation which can be carried out in a short period of time, so that a very firm sleeve arises which is closely modelled to the particular extremity, and which cannot generate any pressure points in the region of the skin, since on consolidation of this structure no radially inwardly directed force arises and there are also no edges or projections which can be formed at the inside.

The cuff-forming cushion is preferably provided with sleeve closure members at its longitudinal edge regions, with the sleeve closure members in particular comprising strip-like burr closure parts.

(Translator's note: The word "burr closure" has been used as a general term to describe a closure typically comprising two types with interengaging hooks and loops which is otherwise only known under the trademark "Velcro" in England).

Accordingly, a sleeve of absolutely correct fitted shape can be generated very simply and rapidly from the initially flat, flexible and easily deformable cuff-forming cushion and initially fixed via the burr closure. After evacuation has taken place a sleeve is present which is consolidated, i.e. has hardened, and is of stabilised shape.

The cuff-forming cushion comprises a material which is transparent to X-rays, in particular a substantially non-extensible plastic foil material in a form friendly to the skin or correspondingly fitted out at the skin side.

Through the choice of a foil material which is essentially non-extensible a substantial contribution is made to the consolidation of the evacuated sleeve since the foil which closely contacts the filling particles cannot be extended and thus a practically rigid structure arises in conjunction with the frictional contact provided between the filling bodies.

The filling particles of the flat cuff cushion which can be deformed into a sleeve comprise, at least in part, particles which overlap one another in an areal manner and which are connected together in force-transmitting manner in the state in which they are pressed against one another, with these particles preferably being at least substantially incompressible. A large choice exists with regard to the filling particles which can be used. However, in making this choice, attention should be paid to the fact that particles should be used which are as light as possible which however in cooperation, i.e. in the pressed together state enclosed between the walls of the cuff-forming cushion, lead to a high overall strength.

At least one perforated region with vacuum-tight edges which permits the passage of extension wires, hoses and the like can be provided in the cuff cushion, so that a wire extension treatment can also take place in the region of the lower limb without difficulties.

In accordance with a preferred embodiment of the invention there a protective sleeve consisting of stable plastic is associated with the flexibly formed sleeve, which is consolidatable under vacuum with the protective sleeve surrounding the vacuum sleeve which then represents an inner sleeve. This protective sleeve can additionally bring about a desired stiffening of the cast.

This plastic sleeve is at least substantially matched to the shape of the relevant extremity of shell-like construction, or so flexibly constructed that it can be applied via a ventral slot. Through this additional stabilisation as a result of the outer plastic sleeve it is also straightforwardly possible to form the entire sleeve apparatus in the manner of a walking plaster.

The plastic sleeve preferably has an inner coating in the form of a hard elastic padding which fills the differently sized spaces between the inner sleeve and the outer sleeve and simultaneously takes on a buffer function against bumps during impact loads.

This outer plastic sleeve can also be fixed via burr closures, so that stepless latching is possible.

The apparatus of the invention can also be formed in the manner of a long thigh plaster or as a stable sleeve which extends from the ankle up to the start of the thigh and it also does not cause any difficulty to effect a construction in the manner of a lower leg resting plaster or walking plaster. Further applications are for example possible with radius fractures to keep the hand and lower arm steady, and also as an upper arm brace for keeping upper arm fractures still, and use is naturally also possible in the manner of an upper arm plaster for holding still the upper arm, the lower arm and the wrist.

It is particularly advantageous to use the apparatus of the invention in conjunction with boots, in particular ski boots, since in contrast to foaming procedures or inflatable inserts a very individual adaptation of the insert is possible which can be tailored to the instantly prevailing circumstances, and indeed while absolutely avoiding regions which exert pressure on the foot.

Particularly advantageous layouts of this possibility of use of the invention are set forth in the claims.

BRIEF DESCRIPTION OF THE DRAWINGS

The invention will be explained in more detail with reference to an embodiment and to the drawing in which are shown.

DESCRIPTION OF THE PREFERRED EMBODIMENTS

Figure 1:
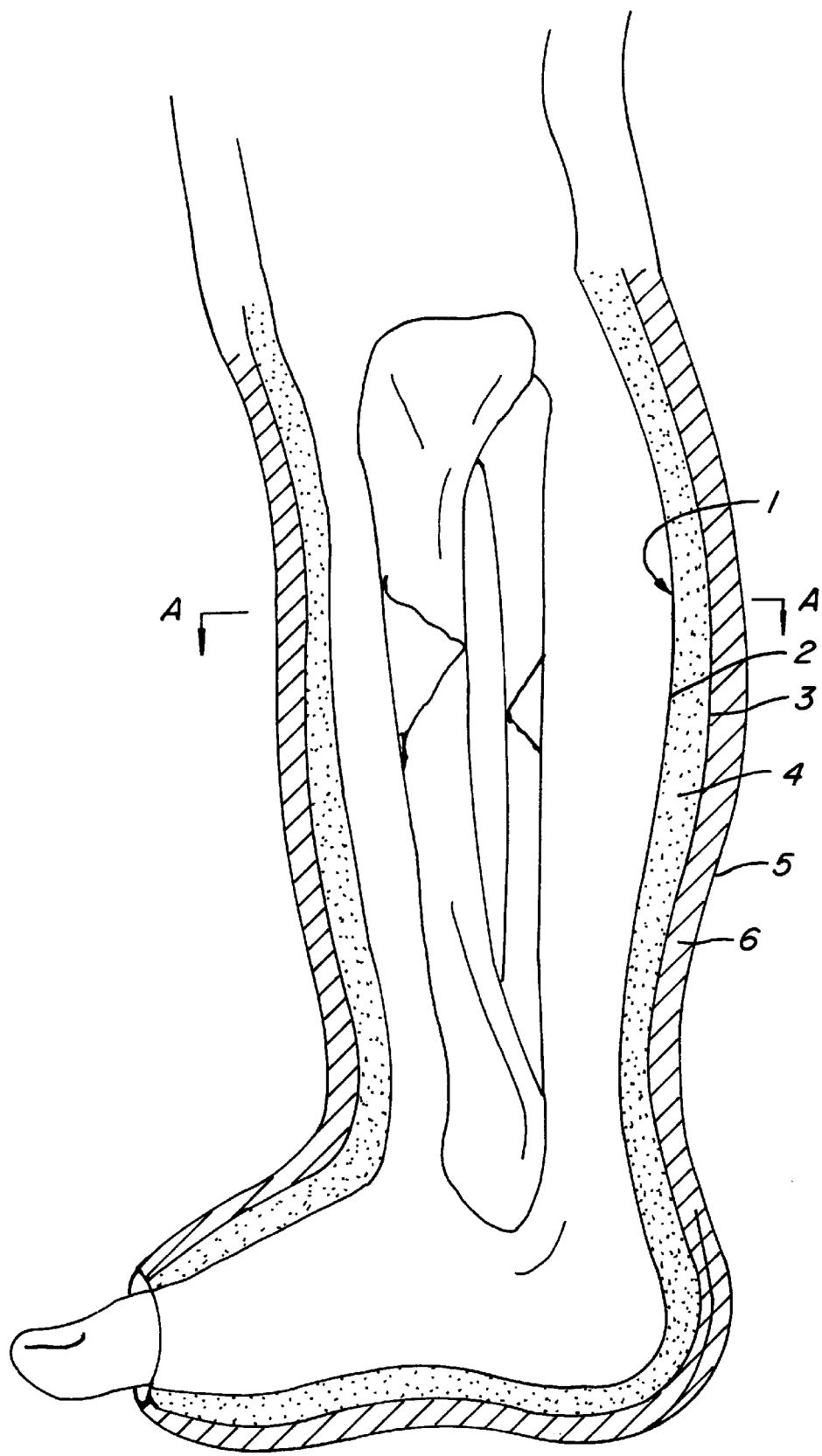
FIG. 1 a schematic longitudinal sectional illustration of a lower limb provided with an apparatus in accordance with the invention, FIG. 2 a schematic part cross-sectional representation of an embodiment of the apparatus of the invention, and FIG. 3 a sectional representation corresponding to the line A—A of FIG. 1.

FIG. 1 shows a lower leg on which an apparatus in accordance with the invention is applied in place of a customary plaster cast.

This apparatus includes a cuff-forming cushion 1 which has been formed into a sleeve and which consists of an inner wall 2 and an outer wall 3 which are made vacuum-tight and are connected together in vacuum-tight manner at their edge regions, and are in particular welded together, so that an inner space arises which is filled with a plurality of individual particulate filling bodies. In this manner a very flat cushion-like and very flexible structure arises which can be laid around the particular limb and can in particular be locked in flush and form fitting manner by means of a burr closure.

Figure 2:
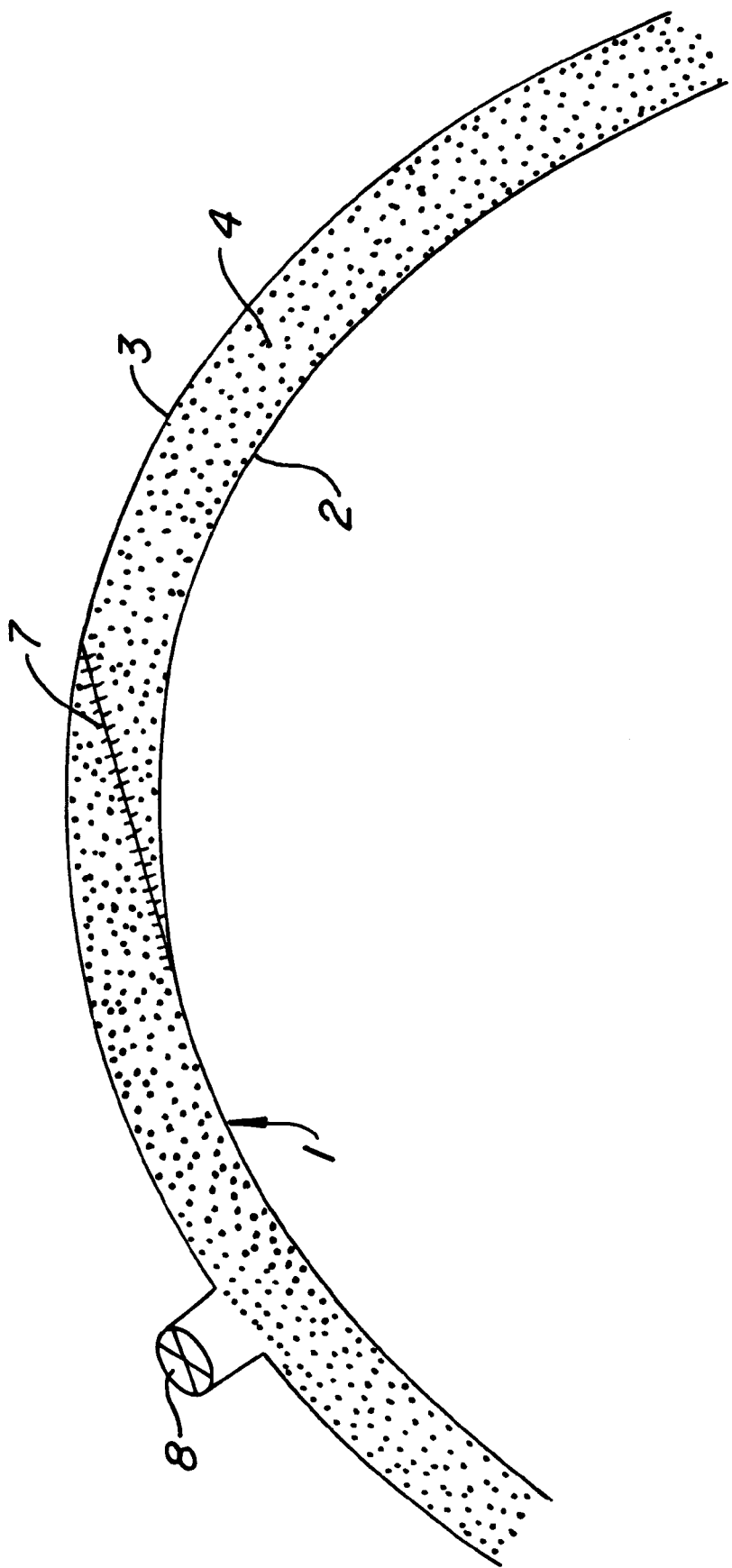

The partly sectioned illustration of FIG. 2 shows the cuff-forming cushion 1 in the region of its connection into a sleeve structure with the edge regions of the cuff-forming cushion being provided with burr closure elements 7 so that with corresponding overlap the basic form of the sleeve structure can also be specified even though the suction process has not yet taken place. At least one evacuation valve 8 is provided to enable an evacuation of the space between the two walls 2 and 3.

After the locking of the plastically well modelled sleeve structure, and after precise alignment of the fractured lower limb and the X-ray check, the required high vacuum in the cuff-forming cushion is generated within a very short time by switching on a vacuum pump which causes the particulate filling bodies to be firmly pressed against one another by the walls 2 and 3 as a result of the differential pressure relative to the atmosphere, so that as a result of the force and form-locked connection a stiff structure arises between the walls 2 and 3 and the filling bodies, with this stiff structure splinting and stabilising the broken lower limb.

For the protection of this structure which stands under vacuum and for further stabilisation an outer plastic sleeve 5 is applied which has approximately the shape of the lower limb and which is of shell-like form or so flexible that application is possible via a ventral slot. The outer plastic sleeve 5 is regionally connected to cushion 1 so that a portion of the cushion, and in particular a portion of its outer wall 3, is not secured to the inner surface of the sleeve. At the inner side of the outer plastic sleeve 5 there is provided a hard elastic padding 6 which fills out the intermediate spaces between the consolidated inner sleeve 1 and the outer sleeve 5, and simultaneously acts as a buffer against blows during impact loads and, for example, provides resistance during walking.

Figure 3:
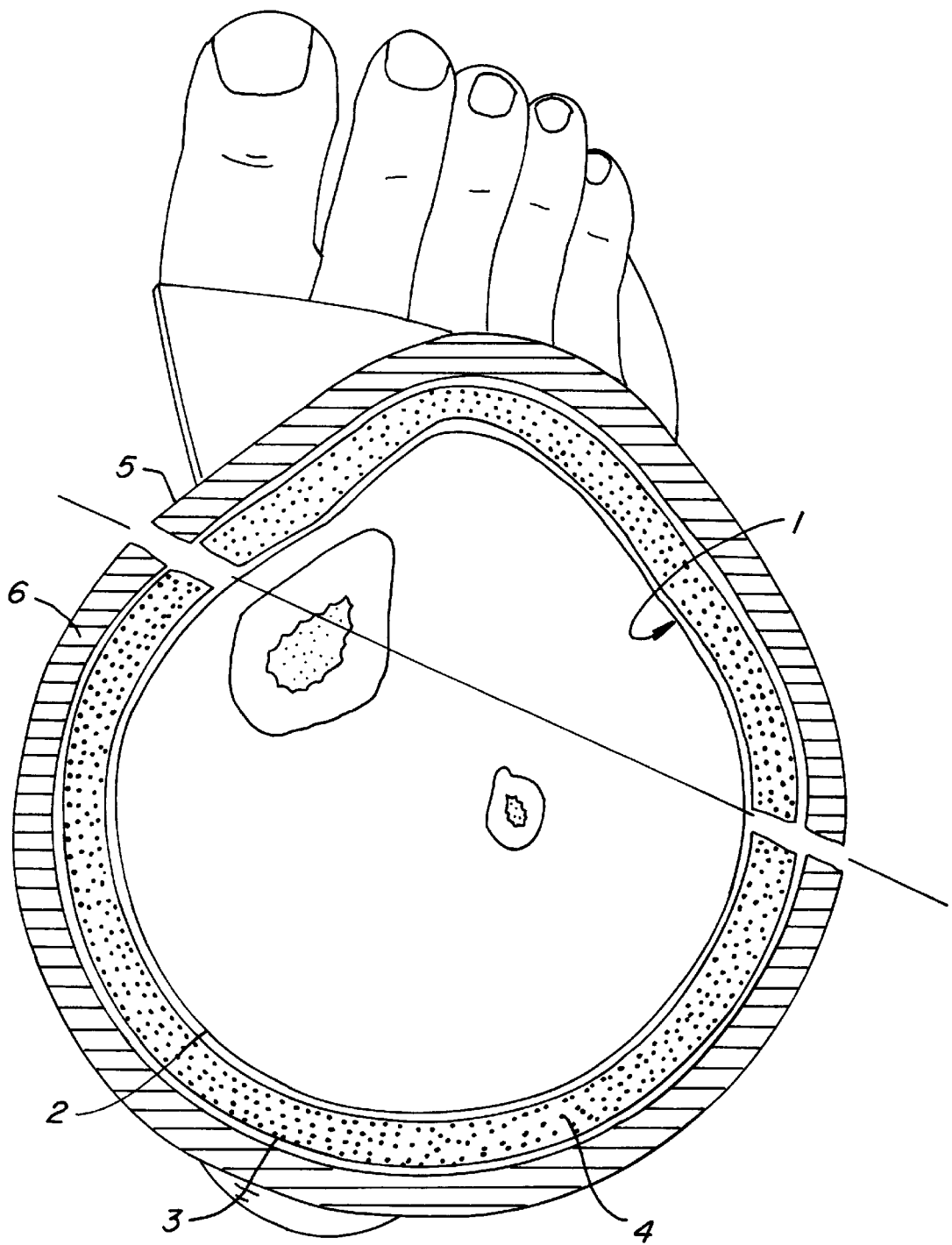

The sectional view of FIG. 3 shows that no disturbing and in particular small area force can be exerted from the consolidated inner sleeve 1 onto the lower limb since the solidification of this sleeve leads during application of the vacuum force to an increase of the clear internal diameter, which has the consequence that a small gap arises between the lower limb and the solidified sleeve.

Alongside the abovementioned advantages it should be pointed out that the apparatus in accordance with the invention can be made sterile so that it is frequently re-usable and contributes to a lowering of the treatment costs. Use in the treatment of open fractures is also in particular possible since a change of the bandages is possible without problem by cancellation of the vacuum and thus the wound is readily accessible. Renewed application is possible within a short period of time. This also leads to the removal of the cast being possible for reasons of hygiene, for example for showering. Above all a tighter application of the cast is possible after loosening of the burr closures and the renewed evacuation when the swelling of the limb being treated goes down in the course of treating the fracture. The change of the plaster cast which would otherwise be necessary is avoided in this manner.

The invention is advantageously usable in the field of the conservative treatment of bridges and also contusions and distorsions of the upper and lower extremities in the specialist field of surgery, accident surgery and orthopaedics.

A particularly interesting field of use for the invention arises in conjunction with boots, in particular ski boots, where it is possible to achieve a differentiated adaptation of the boot to the particular foot, and indeed without providing pressure regions as was frequently the case with customary inserts.

With ski boots it is possible to form the inner boot as a whole as a part which is consolidated under vacuum, however this is not a necessity. In many cases it is of advantage to equip the previously mentioned critical regions with the vacuum cushion of the invention, with this cushion being integrated into the inner boot.

When the inner boot is to be kept very thin then it is also possible to apply the vacuum cushion directly to the outer shoe or to the firm shell, with the shell wall being able to simultaneously form one wall of the cushion. If the vacuum cushions achieve a specific size at which it is possible for the filling bodies to be displaced in undesired manner, then measures can be taken in order to keep the filling bodies at least approximately in their basic position, without however impairing the ready deformability of the cushion so long as the latter has not yet been evacuated.

It is also of advantage that particles or substances can be used as filling bodies which have good insulating properties, since in this way the particularly endangered regions within a ski boot can be advantageously protected against the cold.

What is claimed is:

1. An apparatus for treating a fracture in an extremity comprising a cuff-forming cushion adapted to be formed into a sleeve completely surrounding the extremity, said cushion having an interior wall and an exterior wall defining a vacuum tight inner space therebetween, at least one evacuation valve for evacuating the inner space of said cushion, said evacuation valve being disposed in said exterior wall and adapted to be connected to a vacuum source, a plurality of filling bodies movable relative to one another disposed in the inner space of said cuff-forming cushion, a protective sleeve made of a stable plastic for providing structural support for said cushion and for protecting said cushion when disposed about the extremity against lateral impact, said protective sleeve having a shell-like construction and a shape adapted for wrap-around placement about said cushion when the cushion is placed about and completely surrounds the extremity, only a part of said protective sleeve being connected to said cushion, and means including a burr closure and operatively coupled with said protective sleeve for continuously adjusting an internal diameter of said protective sleeve to adapt the internal diameter to varying sizes of said cushion after the cushion has been applied about and completely surrounds the extremity and evacuated so as to accommodate with said protective sleeve differently sized extremities to which the cushion is applied.

2. An apparatus for treating a fracture in an extremity comprising a unitary cuff-forming cushion adapted to be formed into a sleeve, said cushion having an interior wall and an exterior wall defining a vacuum tight inner space therebetween, at least one evacuation valve for evacuating the inner space of said cushion, said evacuation valve being disposed in said exterior wall and adapted to be connected to a vacuum source, a plurality of filling bodies movable relative to one another disposed in the inner space of said cuff-forming cushion, a protective sleeve made of a stable plastic for providing structural support for said cushion and for protecting said cushion when disposed about the extremity against lateral impact, said protective sleeve having a shell-like construction and a shape adapted for wrap-around placement about said cushion when the cushion is wrapped about the extremity, said protective sleeve being regionally connected to said cushion, and means including a burr closure and operatively coupled with said protective sleeve for continuously adjusting an internal diameter of said protective sleeve to adapt the internal diameter to varying sizes of said cushion after the cushion has been applied about the extremity and evacuated so as to accommodate with said protective sleeve differently sized extremities to which the cushion is applied.

3. Apparatus for treating a fracture in an extremity comprising a generally tubular protective sleeve made of a stable plastic material, being adjustable in its diameter and shaped so that it can be placed about the extremity to which it is to be applied, the protective sleeve including a burr closure for a stepless adjustment of its diameter to thereby vary a diameter of the protective sleeve;

a cushion connected to an inside of the protective sleeve comprising an interior wall and an exterior wall secured to each other to define a vacuum tight inner space between them, the cushion being flexible so that it can be formed into a tubular shape for wrapping the cushion about the extremity and positioning it between the extremity and the protective sleeve;

an evacuation valve carried by the cushion for evacuating the inner space thereof;

a multiplicity of relatively moveable filling bodies disposed in the inner space and between the interior wall and the exterior wall so that, when the cushion is wrapped about said extremity and the interior space is subjected to a vacuum, the cushion and the filling bodies form a substantially rigid, extremity immobilizing tubular sleeve about said extremity; and the exterior wall of the cushion being only regionally secured to the protective sleeve to facilitate the placement of the cushion and of the protective sleeve about said extremity.

4. An apparatus for treating a fracture in an extremity comprising a unitary cuff-forming cushion adapted to be formed into a tubular sleeve wrapped about the extremity and having a longitudinal and circumferential extent, said cushion having an interior wall and an exterior wall defining a vacuum tight inner space therebetween, at least one evacuation valve for evacuating the inner space of said cushion, said evacuation valve being disposed in said exterior wall and adapted to be connected to a vacuum source, a plurality of filling bodies movable relative to one another disposed in the inner space of said cuff-forming cushion and spacing the inner wall from the outer wall over the entire longitudinal and circumferential extend of the sleeve when the vacuum source applies a vacuum to the inner space, a protective sleeve made of a stable plastic for providing structural support for said cushion and for protecting said cushion when disposed about the extremity against lateral impact, said protective sleeve having a shell-like construction and a shape adapted for wrap-around around placement about said cushion when the cushion is placed about the extremity, only a part of said protective sleeve being connected to said cushion, and means including a burr closure and operatively coupled with said protective sleeve for continuously adjusting an internal diameter of said protective sleeve to adapt the internal diameter to a size of said cushion after the cushion has been wrapped about the extremity and evacuated so that said cushion and said protective sleeve can be applied to differently sized extremities, whereby upon the application of the vacuum to the inner space of the cushion a small gap is formed between the inner wall of the cushion and the extremity.

* * * * *